United States Patent [19]

Pardon et al.

[11] 4,350,684

[45] Sep. 21, 1982

[54] **PREPARATION OF *SALMONELLA ABORTUS OVIS* STRAINS AND VACCINE COMPOSITIONS CONTAINING THEM**

[75] Inventors: Pierre Pardon, Tours; Frédéric Lantier, Monnaie; José Marly, Monnaie; Gérard Bourgy, Monnaie, all of France

[73] Assignee: Institut National de la Recherche Agronomique, Paris, France

[21] Appl. No.: 181,809

[22] Filed: Aug. 27, 1980

[30] Foreign Application Priority Data

Aug. 29, 1979 [FR] France ............................... 79 21685

[51] Int. Cl.[3] ........................................... A61K 39/112

[52] U.S. Cl. ........................................................ 424/92

[58] Field of Search .................... 424/92, 93; 435/253, 435/172

[56] References Cited

PUBLICATIONS

Chemical Abstracts, vol. 66, p. 5979, Abst. No. 63774p, 1967.

*Primary Examiner*—Blondel Hazel

*Attorney, Agent, or Firm*—Weiser, Stapler & Spivak

[57] ABSTRACT

The invention relates to the preparation of novel immunogenic agents and compositions of vaccines to combat salmonellosis caused by *Salmonella abortus ovis* and *Salmonella typhimurium*.

The preparation is that of the mutant strains of *Salmonella abortus ovis* and comprises:

(a) the seeding and culture of bacteria from a virulent wild strain, on a medium containing an antibiotic enabling the development of "resistant" mutants;

(b) the culture by replication of the resistant bacteria on a medium free of antibiotic to determine those which are "dependent";

(c) the seeding of the culture of the dependent bacteria derived from (b) on medium free of antibiotic until the appearance of reverse colonies.

The immunogen agents obtained are useful for the preparation of vaccines.

16 Claims, 2 Drawing Figures

PREPARATION OF *SALMONELLA ABORTUS OVIS* STRAINS AND VACCINE COMPOSITIONS CONTAINING THEM

The invention relates to the preparation of novel immunogenic agents and vaccine compositions for combatting salmonellosis caused by *Salmonella abortus ovis, Salmonella typhimurium* and Salmonella strains the antigenic structure of which is similar to the antigenic structure of *Salmonella abortus ovis* and *Salmonella typhimurium*. It relates more particularly to the preparation of novel immunogenic agents and vaccine compositions for combatting salmonellosis caused by *Salmonella abortus ovis*.

*Salmonella abortus ovis* infection attacks small ruminants and notably sheep. This infection is rampant in the endemic state in the large sheep-rearing regions in France and in the majority of sheep-producing countries, where it causes significant losses.

The preventive fight against this disease relies essentially on the use of vaccines constituted from killed *Salmonella abortus ovis*. The innocuousness of this type of vaccine is complete but their efficiency is generally at least considered as being insufficient to comply with the requirements of practice.

The research which has resulted in the invention has the object of providing a non-virulent immunogenic agent, capable of generating a sufficient immune response in the animals to which it is administered, to protect them in an efficient way against *Salmonella abortus ovis* infections.

Another purpose of this research was to produce an agent, having the properties which have just been indicated and which, in addition, is genetically stable and can be prepared in a sufficient amount, that is to say with a yield and under conditions which are compatible with exploitation going beyond the experimental scope of the laboratory.

This research has shown that these results could be reached by means of the immunogenic agents according to the invention. These immunogenic agents are constituted by non-virulent living *Salmonella abortus ovis*, obtained from "wild" virulent strains by the selection of mutants according to their growth aptitudes on media containing an antibiotic, or from strains derived from the first mutants by a second selection, still according to growth criteria on a medium which, this time, is free of antibiotic.

The selection of strains of micro-organisms as a function of growth criteria on media containing an antibiotic, and notably streptomycin, is an operation which has been used for various species with the object, notably, of causing the appearance of strains having attenuated virulence. The results obtained according to this technique are very variable and cannot be foreseen, both as regards the attenuation itself and the modification of other characteristics. This mode of preparation of modified strains is hence not of general application when it is desired to obtain vaccinating strains. Only prolonged tests of the modified strains obtained can permit the determination of their characteristics, and notably their innocuousness and their efficiency for protecting treated animals against infections caused by natural "wild" strains.

In the same way, the genetic stability or again the growth characteristics cannot be foreseen. They can only be known by experimentation. In general, it is known from the prior art that the mutations selected according to these characteristics of growth in a medium with a high concentration of antibiotics are accompanied by a modification in the speed of development of the mutant strains with respect to those of the original strains from which they are derived. The mutant strains have on the whole, a far slower growth. This observation, made for the first mutation, is equally valid for the following mutations produced from the strain of the first mutation.

These prior observations obviously do not encourage research on the mutation of the strains and even more multiple mutations when it is desired to obtain abundant cultures, which are a priori the only ones capable of satisfactory exploitation.

The mutant strains according to the invention are in the first place non-virulent strains selected, from natural virulent strains, for their growth capacity on a medium with a high content of streptomycin, and in addition, which can only be developed satisfactorily in the presence of streptomycin. For this reason, these strains are said to be dependent on streptomycin or "streptodependent" (D). In the second place, the strains according to the invention are more particularly constituted by the mutants selected from the "strepto-dependent" stains and which have the particularity of being able to develop in the absence of streptomycin. These strains are called reverses (Rv).

The natural strains used for preparing the mutant strains according to the invention must be virulent. In fact strains which are non-virulent in a natural way are known. Tests have even been carried out to test the immunogen capacity of these strains. In all the tests of these non-virulent natural strains, it was observed that the protection conferred against infection was nul or very distinctly insufficient, and no vaccine can have been produced from such strains.

Virulent strains used according to the invention for preparing the mutants are "wild" strains, that is to say strains derived from samples taken from animals affected by the infection under natural conditions. The virulent wild strains can generally be used for the preparation of the mutants according to the invention; nonetheless, these strains are not all equivalent and may be differentiated by secondary characteristics important for the use that it is proposed to make of them. Thus, all the wild strains have neither the same degree of virulence nor the same aptitudes to develop.

Various wild strains have been tested among which the strain called "15/5", deposited Aug. 28, 1979 in the National Collection of Micro-organism Cultures in Paris (INSTITUT PASTEUR, 28 rue du Dr Roux, 75015 PARIS) and recorded under n°. I-096, shows both a marked virulence and a rapid growth in quite homogeneous colonies. For this reason, this wild strain is advantageously used according to the invention. However, other wild strains or strains having the same criteriae of virulence and of growth can be used.

The mutant strains prepared according to the invention must be non-virulent, that is to say that, overall, they must not develop pathological phenomena which are similar to those of the infection that they are supposed to prevent in the host animal to which they are administered.

The notion of non-virulence must be stated precisely. It is connected, at least in part, with the characteristics of the development of the micro-organism in the host. Besides, the efficiency of protection conferred is a function of the immune reaction, itself connected with the importance of the development and with the maintainance of the vaccinating micro-organisms in the treated host. In other words, there exists a certain correlation between the efficiency of the protection obtained and a development of the vaccinating bacteria, and a residual virulence is necessary to ensure good protection subsequently.

The difference between the phenomena connected with vaccination and those which correspond to the infection arises from the fact that the development of the vaccinating bacteria remains of limited scope, both in their number and in that of the organs afflicted. This is also manifested, for the treated animal, by the absence of pathological manifestations characteristic of the infection. At the most, the vaccinated animal can show a certain number of momentary rections without a common measure with the infection itself.

For the reasons which have just been specified, it appears that the non-virulence can only be evaluated by in vivo tests directly in the animals of the species which must finally be treated, in the present case these animals are sheep, or on laboratory test animals, (mice, guiena pigs), once the protocol and correlations between the results, in the two cases, have been established. This forms the subject of detailed examples in the following of the description.

The mutant strains according to the invention, of course, must also show an immunogen character which is manifested by a significant protection of the treated animals with respect to *Salmonella abortus ovis* infection. Suitable mutant strains according to the invention are such that their administration to the animal is accompanied by a limited development, which can be detected by bacteriological examinations of the organs and in particular of the spleen, or by the appearance of specific antibodies in an amount very much higher than that which is observed in the untreated animals. In all cases, the immunogen character must be specified by in vivo tests of protection against the infection itself, either on sheep, or on laboratory animals when, as previously for non-virulence, a correlation has been established.

Whatever the strain used, it is self-evident that these virulence characteristics, especially immunogenicity, are connected with the doses used. According to the invention, the immunogen agents are therefore used at doses capable of conferring a significant protection against the infection which is propagated under natural conditions on the treated animals.

The choice of the antibiotic for selecting the mutants according to the invention is guided by reasons of a practical nature. Streptomycin, and more generally, antibiotic agents of the aminoglycoside type (gentamycin, kanamycin . . . ) are known to lead rapidly to the development of resistant strains among the micro-organisms that they are supposed to combat, which moreover constitutes a serious drawback for their use in therapeutics. Other antibiotics lead to similar phenomena, notably sulfonamides, tetracyclines, penicillin, etc.

It is known that resistance to the antibiotic can result from different modification mechanisms. In particular, the genetic modification may affect a chromosome of the bacterium; it may also be located on a DNA extra-chromosomic segment (on a plasmid, for example). The chrosomic modification is a rare event which, once carried out, ensures the stability of the acquired properties. The modification of a plasmid, on the contrary, appears more frequently but is a reversible phenomenon. The characteristic acquired in the latter case does not offer the necessary stability according to the invention. It is absolutely indispensable for the mutant strains not to be able to turn into a virulent form.

It is possible to orient the modification of the strain to one or other of these two types. It is known in fact that, for high concentrations of streptomycin in the medium on which the selection is carried out (concentrations at which this antibiotic is bactericidal and not only bacteriostatic), only chromosomic mutants can be developed. Therefore, to prepare the mutant strains according to the invention, media having a high concentration of streptomycin are selected. Advantageously, this concentration is about 500 μg/ml, but may be much higher, ranging up to 2000 μg/ml and more. This concentration must not be less than that for which the modifications of the selected strains would not be of a chromosomic nature. Advantageously, the medium used for this selection will not contain less than 50 μg/ml.

It is possible to check that the strains obtained have indeed a chromosomic modification and not a transformation of the plasmidic type. Thus, when the original strains and the streptomycin resistant strains are put together, if the second ones have been obtained from a chromosomic mutation, there is no transfer phenomenon of the resistant characteristic from the second ones to the first ones according to the well-known mechanism of conjugation. On the contrary, if the modifications are carried by the extrachromosomic DNA, that is to say that of plasmids or of episomes, the transfer frequency is high. The operational conditions previously indicated for producing mutant strains are selected so that the strains obtained cannot be involved in the transfer of this acquired characteristic of resistance to streptomycin.

What we have just indicated for the mutation resulting in the strepto-resistant characteristic also applies to the following mutations respectively leading to dependant and reverse strains.

The mutation of strains and their selection may be carried out by successive steps in media with an increasing content of streptomycin, but it is possible to directly operate in a medium having the highest concentration which has been selected. The latter manner of proceeding is obviously more convenient. It can be carried out only through the fact that the mutant strains according to the invention have right away a sufficient speed of growth in this medium.

Except the antibiotic, the media in which the selective cultures are carried out have no particular characteristic. Therefore a known medium for enabling the development of the cultures for the species concerned is used. A gelose medium can advantageously be used such as trypticase soya gelose. It is also possible to use selective media for the Salmonella species such as Salmonella-Shigella gelose. Nonetheless, these selective media only have an advantage for preventing accidental contamination and are more useful, for example, for the preservation of the strains or the preparation of compositions intended for vaccination tests.

The other culture conditions are also those which enable good growth.

The selection, isolation and culture of the mutant strains are carried out according to conventional techniques. These techniques take into account in particular the frequency of appearance of the mutation and the greater or lesser capacity of the strains concerned to develop.

The principle of the operations leading to the various mutant strains is as follows.

The wild strain is seeded on the medium containing the antibiotic at the above-indicated concentrations. On this medium, after incubation, colonies appear corresponding to the strains resistant to streptomycin (SR). Culture by replication of the resistant colonies on a medium devoid of streptomycin enables the determination, among these resistant colonies, of those which are dependent (D) by comparison of the replicated culture with the culture on the medium containing streptomycin.

The dependent strains, once they have been identified, are isolated and cultivated according to conventional methods.

Starting from dependent strains, procedure is similar for selecting the so-called reverse strains.

The medium free from streptomycin is seeded by means of dependent strains. The colonies which are developed under these conditions are mutants of the dependent strains (and not the initial wild strains). A very high proportion of the reverse strains obtained by this second selection does not develop on the medium containing streptomycin.

The reverse strains obtained are also isolated and preserved.

The mutant strains obtained according to the invention and within the same group, dependent or reverse, do not have uniform characteristics apart from that which enables them to be selected. Thus it has been indicated that, among the reverse strains, certain strains could develop in media containing streptomycin or in media containing no streptomycin.

Another characteristic appears in certain dependent colonies. Ordinarily, cultures of Salmonella, whether they are wild, dependent or reverse, are constituted from well individualized cells which can be isolated from one another. There may appear nonetheless in certain cases, dependent strains in which growth of the bacteria occurs without the cells being systematically separated. The culture observed under the microscope is then formed from clusters or small chains of bacteria linked to one another.

The appearance of these strains of incompletely individualized bacteria is disadvantageous. In fact, for utilization as a vaccine strain, it is preferred to use quite homogeneous strains and at predetermined doses. The presence of these chains is adverse to the achievement of these two conditions.

Contrary to what could have been expected to be observed, the reverse strains obtained according to the invention, resulting from two successive mutations, have a growth level which can be compared to the one of the dependent strains which, themselves, have only undergone a single mutation. The in vitro growth of reverse strains is even better than the one of the dependent strains which have only undergone a single mutation; the culture of reverse strains does not require the use of streptomycin in the culture medium.

By way of indication, on their respective culture medium, it is possible to compare the growth level of a wild strain and of mutant strains which are derived therefrom, by the time necessary after seeding, for the formation of colonies one millimeter in diameter. It has thus been possible to observe, for the wild strain 15/5 which develops rapidly, a time of about 24 hours. The dependent strains obtained from the strain 15/5, to reach the same development, had to be cultivated for about 72 hours, and reverse strains for about 48 hours.

If the reverse or dependent strains can be obtained under similar conditions of yield and facility, the choice of a given type is a function of other particularities. Thus the dependent strains cultivated on a medium with a high content of antibiotic include, within the bacteria, a certain amount of this same antibiotic. The preparation of polyvalent vaccines, that is to say of vaccines containing several viable immunogenic agents, may consequently be thwarted. The presence of streptomycin carried by the dependent Salmonella resists, in fact, the combination with other living micro-organisms sensitive to this antibiotic. With the reverse strains, this possible drawback is obviously avoided.

The reasons which guide the choice between dependent and reverse strains are also related to the in vivo efficiency. On this point, as the examples given below show, no very marked difference appeared between these two categories. Overall, the differences observed on the group of strains of one category with respect to the group of strains of the other category are less important than those which may appear between two strains of the same category. If the "best" strains of each category are compared, it seems that the reverse strains are more immunogen but also more virulent, these characteristics, as we have said, being generally connected.

From the theoretical point of view, this advantage in favor of certain reverse strains can be explained perhaps by the very nature of these strains. The dependent strains administered to the host occur in a medium which is not favorable to their development because of the lack of antibiotic. The micro-organisms continue to grow because of the presence of streptomycin contained in the interior itself of the cells administered, but, the amount of antibiotic becoming smaller and smaller, the growth of the dependent bacteria is necessarily limited. There is nothing similar as regards the reverse strains which can hence be better propagated and, consequently account for a better immune response. The results of tests seem to confirm this hypothesis.

Another advantage in favor of certain reverse strains is connected with the possibility of distinguishing them from other strains of Salmonella by a simple conventional identification test. The test, called the Voges-Proskauer test, is used in test batteries for identifying enterobacteria. This test is negative for natural Salmonella strains.

Contrary to this general character, some of the reverse strains which have been tested revealed themselves to be positive. This, accessorily, enables the reverse strains to be distinguished from the natural strains from which they are derived, the principal distinction remaining the very different growth speeds.

The Voges-Proskauer test is not applicable to dependent strains. This test which is sensitive to acidity, is positive for all these strains by reason of the presence of streptomycin.

In all the foregoing, it is to be concluded that, once the dependent or reverse strains are prepared as has been indicated, it is necessary to subject these strains to a test protocol to ensure their efficiency and their innocuousness. This protocal according to the invention comprises the administration, to mice, of a test dose of the strain which is studied. This test dose is selected with respect to the dose of virulent wild strain which is lethal for the mice. The strain which is studied, at the dose concerned, must not cause the death of the animals, but on the other hand, must develop in a limited manner, which is characterized notably by the presence of the bacteria of this strain in certain organs of the test animals. The studied strain which is administered to test animals must, in addition, improve the resistance of the test animals with respect to infection caused by direct inoculation of wild bacteria.

The results of tests which have been carried out on mice are in addition advantageously confirmed by tests on sheep. In these animals, different measurements of the immunogenic activity may be followed: serological measurements for detecting the presence of specific antibodies (which measurements have the advantage of not necessitating the slaughtering of the test animals), bacteriological measurements for the detection of vaccinating bacteria in various tissus (spleen, lymph nodes, nodules . . . ).

By following this test protocol, it is possible to appreciate, among the mutant strains prepared according to the invention, those which are most suited to protect the vaccinated animals against infection caused by *Salmonella abortus ovis*.

Taking into account the various factors considered above, a strain according to the invention which is particularly advantageous is a reverse strain which is denoted in the examples under the name $Rv_6$, which strain was deposited on Aug. 28, 1979 in the National Collection of Micro-organisms in Paris (INSTITUT PASTEUR) and registered under n°I-097.

The reverse strain $Rv_6$ is Voges-Proskauer negative.

This reverse strain $Rv_6$ can be identified, for example, either by its sensitivity to streptomycin, or by the culture media on which it is able to grow.

As regards the sensitivity to streptomycin, this reverse strain is sensitive to a low concentration of streptomycin in the culture medium. This concentration at which $Rv_6$ is sensitive is less than 50 μg/ml, is as low as about 10 μg/ml and is comprised between about 5 μg/ml and about 10 μg/ml, whereas a concentration of streptomycin necessary to inhibit other natural tested strains of *Salmonella abortus ovis* can amount to 50 μg/ml.

As regards the culture media on which $Rv_6$ can grow, the use of growth factors such as vitamins and aminoacids added to a minimal culture medium enables to distinguish and identify the needs of the strain $Rv_6$ from the needs of the strain 15/5 as well as from the needs of other natural tested strains of *Salmonella abortus ovis*.

The minimal culture medium used is known in the name of "Minimal Agar of Davis" and is the "Minimal Agar of Davis" manufactured by DIFCO Laboratories, Detroit, Mich., USA. As respect to the growth factors which can be added into this minimal culture medium, the amounts of said growth factors are to be found for example in the following reference "Experiments in Microbial Genetics" by Clowes R. C., and Hayes W., edited by Blackwell Scientific Publication, Oxford-Edinburgh.

For the purpose of the identification of the strain $Rv_6$, glucose, valin and nicotinic acid are added to the medium "Minimal Agar of Davis"; the culture medium thus obtained being hereunder designated by "common culture medium".

Growth factors are selected from among the group comprising methionine, thiamin and sodium thiosulphate, at least one of the three compounds being added into the common culture medium which has just been defined.

Five culture media are then prepared, the composition of each of these media being respectively ---
1° common culture medium + methionine
+ thiamin
+ sodium thiosulphate
2° common culture medium + thiamin
+ sodium thiosulphate
3° common culture medium + methionine
4° common culture medium + thiamin
5° common culture medium + sodium thiosulphate.
---

The growth of different strains is tested on each of these five above defined media, the symbol "+" meaning that the strain is able to grow, and the symbol "−" meaning that the strain is not able to grow.

The results obtained for each culture medium enable to identify and distinguish $Rv_6$ from *Salmonella abortus ovis* (15/5) on the one hand and from 59 other natural strains of *Salmonella abortus ovis* which have been tested.

The table hereunder gathers the results.

| Strains | "Minimal Agar of Davis" + glucose + valin + nicotinic acid } "Common culture medium" | | | | |
|---|---|---|---|---|---|
| | Methionine Thiamin Sodium thiosulphate | Thiamin sodium thiosulphate | Methionine | Thiamin | sodium thiosulphate |
| *Salmonella abortus ovis* 15/5 | + | + | ±(2) | + | − |
| $Rv_6$ | + | + | ±(2) | − | − |
| 59 other strains of *Salmonella abortus ovis* | + | −(1) | + | − | −(3) |

(1)58 strains out of 59 do not grow; a single strain grows, behaving as an exception with respect to non growing.
(2)Weak growth of the strains which can be clearly distinguished from the growth indicated by "+".
(3)58 strains out of 59 do not grow; a single strain behaves as an exception with respect to non growing; it is the same strain as the one which grows on the Minimal Agar of Davies + glucose + valin + nicotinic acid into which thiamin and sodium thiosulphate have been added.

From dependent or reverse mutant strains, immunogen compositions according to the invention for the preventive treatment of *Salmonella abortus ovis* infection are prepared.

The vaccinating compositions may of course be constituted by means of freshly cultivated bacteria, but, for obvious reasons of facility of preservation, they are preferably prepared by means of bacteria which are freeze-dried after culture.

To administer the vaccinating bacteria, the medium in which they are suspended is not critical. Of course, this medium must not interfere with the good viability of the bacteria that they contain. Its exact composition, in the same way as the volume administered, are a function of the mode of administration. The latter may take very varied forms: parenteral administration (intradermal, intramuscular), conjunctival instillation, oral administration, etc.

To each of these modes there corresponds a vehicle and if necessary conventional appropriate adjuvants.

A preferred vehicle for parenteral administration is constituted by a physiological saline solution. The suspension is in this case advantageously prepared extemporaneously from freeze-dried bacteria.

The dosages used to vaccinate the sheep vary according to the mode of administration and according to the strains; they are estimated as a function of the results of the test protocol of the strain which is concerned. The dose is selected so that the protection conferred on the treated animal is significant and does not cause any adverse reaction.

For administration by the parenteral route of bacteria of dependent or reverse strains according to the invention, preferred doses are those comprised between about $1 \times 10^7$ and $5 \times 10^9$ living bacteria, and preferably about $7 \times 10^8$ bacteria. For administration by the oral route, the doses administered must be substantially higher and may amount to $10^{10}$ bacteria.

The vaccinating compositions may also contain other immunogen agents, the administration of which is compatible with that of the vaccinating bacteria according to the invention, so as to constitute polyvalent vaccines. Polyvalent vaccines of this type may notably be constituted in order to carry out a simultaneous preventive treatment for several infections caused by enterobacteria of various species.

The following examples of the preparation, selection, and culture of the vaccinating strains according to the invention, as well as the inocuousness and efficiency tests of these strains illustrate the invention in a more detailed manner.

1. Choice of initial strains

The *Salmonella abortus ovis* used for the production of the vaccinating strains according to the invention are virulent natural strains. These strains are taken from infected animals identified on the occasion of abortions.

The starting natural strains which are used must have a certain degree of virulence.

The choice of the natural strains hence comprises a prior virulence test. Thus the determination of the lethal doses and the infecting doses for different strains identified by the laboratory numbers was thus carried out.

In the table below, the results of these tests, in which the bacteria are administered to $CD_1$ mice, by plantar subcutaneous injection, are gathered.

| Strains *Salmonella abortus ovis* | $LD_{50}$ | $ID_{50}$ |
|---|---|---|
| S 15/5 | $5\times10^7$ | $2\times10^3$ |
| S 7 | $3\times10^7$ | $9\times10^2$ |
| S 8 | $2\times10^8$ | $5\times10^3$ |
| S 9 | $9\times10^7$ | $1\times10^3$ |
| S 10a | $9\times10^7$ | $1\times10^3$ |
| S 12a | $9\times10^7$ | $7\times10^2$ |

Besides the virulence criteria, the strains selected have preferably growth characteristics which make their use convenient. The strain called 15/5 offers a relatively fast growth and quite homogeneous colonies. These two properties make the identification and recognition, as well as the selection of derived mutant strains easy.

2. Selection and isolation of mutant strains

The strain 15/5, taken for its growth qualities, was passed on to a medium rich in streptomycin. The medium was trypticase-soya gelose containing 500 μg/ml of streptomycin. On this medium, the so-called strepto-resistant strains develop.

The frequency of appearance of the strepto-resistant strains is about 1 per $2\times10^8$ bacteria. These strains are replicated by conventional techniques on media containing streptomycin and simultaneously on media without streptomycin.

It is thus observed that about 2% of the strepto-resistant strains do not develop or develop very little on the media devoid of streptomycin. These strains are isolated and cultivated, and constitute the so-called "strepto-dependent" strains.

The strepto-dependent strains are in their turn cultivated as a large number of clones in media devoid of streptomycin to establish the appearance of colonies which are no longer "dependent". As a rule, the "reverse" strains, which are no longer dependent on streptomycin, have lost the aptitude to develop on media containing streptomycin.

In the preparation of the cultures, a non-specific culture medium, trypticase-soya gelose is utilized (Trypticase-soy-agar, marketed by the MERIEUX Company). For the bacteriological examinations in which it is necessary to prevent the presence of foreign bacteria, the medium formed by Salmonella Shigella gelose (marketed by the PASTEUR INSTITUT) is utilized.

The table hereafter recapitulates the media used according to the strains and their destination.

| | Culture media used for | |
|---|---|---|
| Strains | preparation of the inoculums | bacteriological examinations |
| Wild 15/5 | TSA (3) | SS (4) |
| Mutants D (1) | TSA (5) and TSA + streptomycin (6) | SS (5) and SS + streptomycin (6) |
| Mutants Rv (2) | TSA | SS |

(1) Streptomycin-dependent strains
(2) Reverse strains
(3) Trypticase-soya gelose (Trypticase-soy-agar, B-D MERIEUX)
(4) *Salmonella Shigella* gelose (PASTEUR INSTITUT)
(5) Used to check streptomycin-dependence
(6) 500 μg per milliliter of medium The growth characteristics of the various strains are summarized in the following table.

| | Growth on medium | |
|---|---|---|
| Strains | with strepto. (1) | without strepto. |
| SR (3) | + | + |
| D | + | − |
| Rv | − (2) | + |

(1) 500 μg/ml of medium
(2) Exception: the $Rv_5$ strain grows under these conditions
(3) SR = streptomycin resistant strain

3. Tests of the virulence of mutant strains in mice

The residual virulence of several dependent and reverse strains, obtained according to the methods described above, is compared with that of the wild strain 15/5 from which they are derived. The comparative tests have first been carried out on two breeds of mice having a different sensitivity with respect to wild strains of *Salmonella abortus ovis*.

Experiment on $CD_1$ mice

The virulence of the strains was evaluated by their capacity to cause the death of the inoculated mice, or to colonize their spleen.

Adult female mice, of $CD_1$ breed (Charles RIVERS, France), in groups of 20, were inoculated by the intraperitoneal route as indicated in the table below.

| Strains | Dose (per animal) | Number of dead mice (20 mice/batch) | Mean weight of spleens* in g $\left(\pm \frac{s}{\sqrt{n}}\right)$ |
|---|---|---|---|
| 15/5 | $2,2 \times 10^7$ | 7 | — |
| $D_1$ | $2,8 \times 10^7$ | 0 | $0,33 \pm 0,03$ |
| $D_2$ | $2,4 \times 10^7$ | 0 | $0,34 \pm 0,02$ |
| $D_3$ | $1,5 \times 10^6$ | 0 | $0,16 \pm 0,01$ |
| $D_4$ | $1,5 \times 10^6$ | 0 | $0,16 \pm 0,01$ |
| $D_5$ | $1,5 \times 10^7$ | 0 | $0,40 \pm 0,02$ |
| $D_6$ | $2,4 \times 10^7$ | 0 | $0,34 \pm 0,03$ |
| $Rv_1$ | $2,6 \times 10^7$ | 0 | $0,49 \pm 0,02$ |
| $Rv_2$ | $2,1 \times 10^7$ | 0 | $0,48 \pm 0,02$ |
| $Rv_3$ | $2,2 \times 10^7$ | 0 | $0,44 \pm 0,03$ |
| $Rv_4$ | $2,2 \times 10^7$ | 0 | $0,43 \pm 0,03$ |
| $Rv_5$ | $9,8 \times 10^6$ | 0 | $0,38 \pm 0,03$ |
| $Rv_6$ | $2,2 \times 10^7$ | 0 | $0,46 \pm 0,04$ |
| $Rv_7$ | $2,8 \times 10^7$ | 0 | $0,46 \pm 0,02$ |
| $Rv_8$ | $1,8 \times 10^7$ | 0 | $0,46 \pm 0,03$ |

*Calculated for batches in which all the mice survived 6 days after the inoculation.

Seven mice in the 20 inoculated with the wild strain 15/5 were dead 6 days after the inoculation; at this date, the surviving animals of this group were all very much clinically affected. In the other batches, all the mice survived and manifested few or no clinical signs at the time of slaughtering; spleens of the animals inoculated with the reverse strains were mostly larger than those of the animals inoculated with dependent strains.

The test was renewed by carrying out the inoculation by the plantar subcutaneous route.

The spleens of the $CD_1$ mice, taken 6 days after the inoculation, were less frequently and less intensely colonized by the mutant Salmonella than by the wild strain 15/5. The results are shown in the following table.

| Strains | Dose (per animal) | Number of infected spleens (8 mice/batch) | Splenic infection (1) $\left(\log X \pm \frac{s}{\sqrt{n}}\right)$ |
|---|---|---|---|
| 15/5 | $8,8 \times 10^5$ | 8 | $3,16 \pm 0,2$ |
| $D_1$ | $8,1 \times 10^5$ | 1 | 1,18 |
| $D_2$ | $5,4 \times 10^5$ | 1 | 0,7 |
| $D_3$ | $2,6 \times 10^5$ | 0 | — |
| $D_4$ | $3,0 \times 10^5$ | 0 | — |
| $D_5$ | $5,2 \times 10^5$ | 3 | 0,53 |
| $D_6$ | $4,4 \times 10^5$ | 0 | — |
| $Rv_1$ | $5,0 \times 10^5$ | 3 | 0,4 |
| $Rv_2$ | $6,2 \times 10^5$ | 0 | — |
| $Rv_3$ | $4,8 \times 10^5$ | 1 | 0 |
| $Rv_4$ | $4,8 \times 10^5$ | 2 | 0,3 |
| $Rv_5$ | $6,2 \times 10^5$ | 4 | 0,7 |
| $Rv_6$ | $4,5 \times 10^5$ | 5 | 0,64 |
| $Rv_7$ | $4,2 \times 10^5$ | 1 | 0 |
| $Rv_8$ | $6,7 \times 10^5$ | 3 | 0,10 |

(1) Average of $\log_{10}$ of the numbers of Salmonella; the uninfected spleens were not taken into account for the calculation of the average.

Experiment on $OF_1$ mice

The mice of $OF_1$ breed (Iffa Credo) are known for being more sensitive to infection after parenteral inoculation of *Salmonella abortus ovis* than $CD_1$ mice.

(a) Tests similar to the preceeding ones were carried out on these mice to demonstrate more clearly the virulence of the different strains.

Adult female $OF_1$ mice were inoculated by the plantar subcutaneous route to compare the strains according to their lethal power and their capacity to colonize the spleen and the poplitial ganglion draining the site of injection. The mice were sacrified and autopsied 6 days after the inoculation.

The following table recapitulates the results of these tests. It is observed, as previously, that there is a total absence of mortality in animals inoculated by means of mutant strains prepared according to the invention, and, on the whole, the administration of reverse strains seems to be accompanied by more marked effects.

| | | | Poplitial Ganglions | | Spleens | | |
|---|---|---|---|---|---|---|---|
| | | | | | | Infection (1) | Weight (2) |
| Strains | Dose | Survivors total | infected total | Infection (1) | Infected total | $\left(\log X \pm \frac{s}{n}\right)$ | in g $\left(\pm \frac{s}{\sqrt{n}}\right)$ |
| 15/5 | $2,6 \times 10^6$ | 4/8 | | | | | |
| $D_1$ | $7,5 \times 10^6$ | 8/8 | 8/8 | $2,29 \pm 0,11$ | 8/8 | $0,80 \pm 0,09$ | $0,07 \pm 0,01$ |
| $D_2$ | $5,5 \times 10^6$ | 8/8 | 8/8 | $2,51 \pm 0,05$ | 8/8 | $1,55 \pm 0,14$ | $0,07 \pm 0,01$ |
| $D_3$ | $1,4 \times 10^6$ | 8/8 | 8/8 | $2,05 \pm 0,10$ | 7/8 | $0,21 \pm 0,11$ | $0,09 \pm 0,01$ |
| $D_4$ | $5,5 \times 10^6$ | 8/8 | 8/8 | $1,41 \pm 0,10$ | 5/8 | $0,80 \pm 0,17$ | $0,09 \pm 0,00$ |
| $D_5$ | $9,0 \times 10^6$ | 8/8 | 8/8 | $2,75 \pm 0,06$ | 8/8 | $1,52 \pm 0,17$ | $0,07 \pm 0,00$ |
| $D_6$ | $2,9 \times 10^6$ | 8/8 | 8/8 | $2,24 \pm 0,05$ | 6/8 | $0,46 \pm 0,13$ | $0,07 \pm 0,01$ |
| $Rv_1$ | $4,0 \times 10^6$ | 8/8 | 8/8 | $3,18 \pm 0,09$ | 8/8 | $3,87 \pm 0,21$ | $0,16 \pm 0,02$ |
| $Rv_2$ | $4,7 \times 10^6$ | 8/8 | 8/8 | $2,66 \pm 0,05$ | 8/8 | $1,46 \pm 0,14$ | $0,07 \pm 0,01$ |
| $Rv_3$ | $5,5 \times 10^6$ | 8/8 | 8/8 | $3,01 \pm 0,08$ | 8/8 | $1,14 \pm 0,14$ | $0,08 \pm 0,01$ |
| $Rv_4$ | $5,5 \times 10^6$ | 8/8 | 8/8 | $2,92 \pm 0,07$ | 8/8 | $3,64 \pm 0,19$ | $0,20 \pm 0,02$ |
| $Rv_5$ | $4,2 \times 10^6$ | 8/8 | 8/8 | $2,69 \pm 0,10$ | 7/8 | $1,02 \pm 0,16$ | $0,10 \pm 0,01$ |
| $Rv_6$ | $6,5 \times 10^6$ | 8/8 | 8/8 | $2,95 \pm 0,12$ | 8/8 | $3,88 \pm 0,20$ | $0,21 \pm 0,02$ |
| $Rv_7$ | $4,8 \times 10^6$ | 8/8 | 8/8 | $2,88 \pm 0,15$ | 8/8 | $2,05 \pm 0,24$ | $0,10 \pm 0,01$ |
| $Rv_8$ | $3,4 \times 10^6$ | 8/8 | 8/8 | $2,56 \pm 0,17$ | 8/8 | $1,84 \pm 0,11$ | $0,08 \pm 0,01$ |

(1) Average of the decimal logarithms of viable Salmonella per organ, calculated from organs taken from the experimental groups without mortality
(2) Average weight, in grams, of the spleens of mice forming part of the experimental groups without mortality All the mutant strains obtained manifest a substantially weaker virulence in $CD_1$ or $OF_1$ mice than that of the wild 15/5 strain.

(b) The relative effect of inoculation in time of the wild strain, of a dependent strain and of a reverse strain, on the weight of the spleen and its colonization by Salmonella have also been determined.

Three batches of 35 adult female $OF_1$ mice were inoculated by the intraveinous route with about $1 \times 10^6$ viable bacteria from 15/5, $D_5$ or $Rv_6$ strains. On the days indicated in the accompanying Figures, 5 mice from each batch were killed and the spleens were taken out, weighed and placed in culture.

Figure 1:
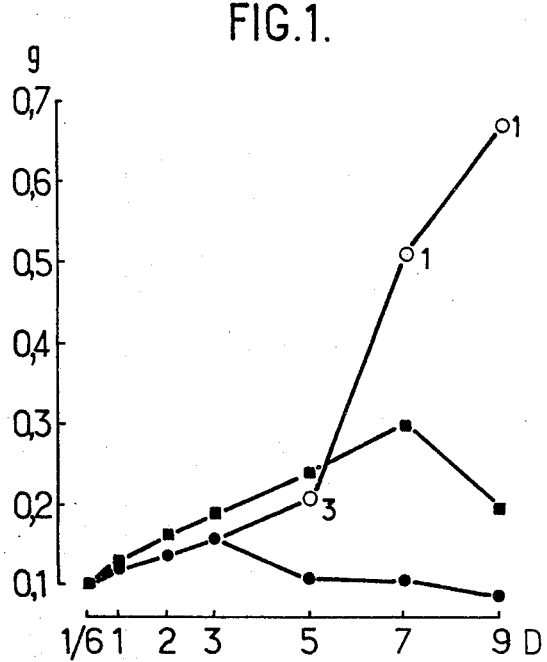
FIG. 1 shows the development of the average weight of the spleen in grams, as a function of the time indicated in days.
Figure 2:
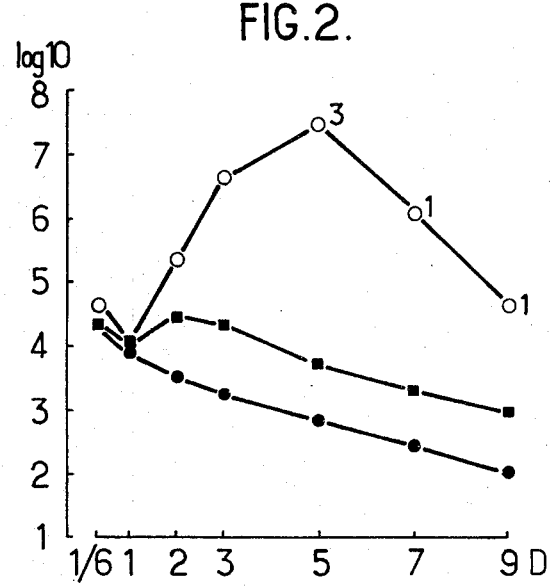
FIG. 2 shows the development of the average of $\log_{10}$ of the number of Salmonella/spleen as a function of time.

The Figures plotted in the graphs indicate the number of surviving mice when the latter is less than 5.

The development of the spleen infection and that of the weight of the spleen enable the conclusion of the low residual virulence of the mutant strains $D_5$ and $Rv_6$. In the spleen, the number of mutant bacteria gradually decreases. The $Rv_6$ bacteria persist in this organ longer and in greater number than the $D_5$ bacteria. In addition, the splenomegaly developed after inoculation of the $Rv_6$ is higher and more lasting than that observed after inoculation of the $D_5$ strain.

(4) Tests of immunogenicity in the mouse

To appreciate the immunogen power of the mutant strains according to the invention, the resistance to a test inoculation was measured in adult female mice of the $CD_1$ breed, either unvaccinated, or vaccinated with one of the mutant strains.

A period of 3 weeks separates the vaccination, on the one hand, and a test of the mice, on the other hand.

The test bacteria were strepto-resistant 15/5 *Salmonella abortus ovis* (SR). They were inoculated by the plantar subcutaneous route at the dose of $4.8 \times 10^5$ viable bacteria per animal. The virulence of this strain for the mouse is of the same order as that of the wild 15/5 strain from which it is derived by selection on a medium containing 500 µg/ml of steptomycin.

Vaccination with bacteria of attenuated virulence has the effect of reducing the number of bacteria colonizing the spleen 7 days after the test inoculation. This overall effect must be qualified: differences appear according to the vaccinal strains.

| Mice | Vaccinal strain | Vaccinal doses (per animal) (1) | Infected spleens/ Cultivated spleens | Splenic infection $\left(\log X \pm \dfrac{s}{\sqrt{n}}\right)$ (2) |
|---|---|---|---|---|
| Controls | — | — | 6/6 | 4,05 ± 0,44 |
| Vaccinated | $D_1$ | $8,3 \times 10^5$ | 6/6 | 3,56 ± 0,43 |
| | $D_2$ | $7,0 \times 10^5$ | 6/6 | 3,27 ± 0,28 |
| | $D_3$ | $3,3 \times 10^3$ | 6/6 | 3,72 ± 0,36 |
| | $D_4$ | $4,6 \times 10^5$ | 6/6 | 3,09 ± 0,29 |
| | $D_5$ | $9,5 \times 10^5$ | 6/6 | 3,38 ± 0,25 |
| | $D_6$ | $1,0 \times 10^6$ | 6/6 | 3,68 ± 0,15 |
| | $Rv_1$ | $6,4 \times 10^5$ | 5/6 | 2,87 ± 0,08 |
| | $Rv_2$ | $5,0 \times 10^5$ | 6/6 | 3,36 ± 0,09 |
| | $Rv_3$ | $5,5 \times 10^5$ | 6/6 | 2,48 ± 0,63 |
| | $Rv_4$ | $4,7 \times 10^5$ | 6/6 | 3,44 ± 0,20 |
| | $Rv_5$ | $4,5 \times 10^5$ | 6/6 | 2,84 ± 0,47 |
| | $Rv_6$ | $4,8 \times 10^5$ | 4/5 (3) | 2,38 ± 0,53 |
| | $Rv_7$ | $6,0 \times 10^5$ | 6/6 | 3,43 ± 0,64 |
| | $Rv_8$ | $3,7 \times 10^5$ | 6/6 | 4,05 ± 0,27 |

(1) Injection by the sub-cutaneous route in the neck.
(2) Average of the decimal logarithms of the number of viable Salmonella per organ; calculation from organs taken out 6 days after the test inoculation (SR).
(3) One mouse accidentally died in the course of the experiment.

(5) Virulence tests on rams.

A test was carried out, to evaluate the residual virulence of the mutant strains according to the invention on rams.

The tests on rams have the advantage, with respect to those which have been carried out on ewes, of not being influenced by pregnant periods. To this purpose, the development of the rectal temperature, of the thickness of the skin fold at the site of the injection and of the serological response was followed. The distribution of the Salmonella in the organism was also studied.

Twenty-one rams, 7 to 8 months old, received, by the sub-cutaneous route on the ribs behind the right elbow, variable doses of the wild strain 15/5 or of the mutant strains. The rams were slaughtered twelve days after the vaccine injection. The removal of the organs and ganglions took place on autopsy.

The doses of vaccines were prepared by culture at 37° C. for 24 hours on trypticase soya gelose (B-D MERIEUX) inclined in tubes, containing or not containing streptomycin (500 µg/ml). The culture was harvested in isotonic saline solution; the suspension obtained was adjusted by photometric measurement at the desired concentration, then the concentration of viable bacteria was checked by seeding after dilution.

The ganglions which were taken out in the slaughterhouse were degreased, singed superficially, cut over their whole perimeter and crushed mechanically in a sterile sachet containing a small volume of sterile saline solution. The liquid containing the ganglionic juice which was thus expressed, was seeded in the proportion of 0.2 ml per dish of medium.

The organs or pieces of organs taken out at the slaughterhouse were singed superficially, then ground. An aliquot of each ground material was spread over the culture medium. The excess of ground material was removed after spreading.

The reaction nodules were dissected, singed superficially and crushed. The liquid obtained was seeded on a dish of culture medium.

Five blood samplings, at intervals of 2 or 3 days, were carried out during the 12 days separating the vaccine injection and the slaughtering of the animals. The seroagglutination test was done by the microtechnique on plates, using antigen "O" (surface antigen) prepared from the 15/5 strain and titrated with respect to a serum used as a reference for the laboratory. The agglutinating titers are expressed by the order number of the last dilution (to one half) which is positive, the number 1 corresponding to the final dilution at 1/10 of the serum under test.

It appears that the mutant strains cause substantially weaker biological reactions than the 15/5 wild strain. Among the mutant strains, the reverse strains seem more "active" than the dependent strains.

| Vaccination | | Acmes | Skin fold | Weight PSD | Salmonella present in | | Other samplings | Agglutinating titer maxima |
|---|---|---|---|---|---|---|---|---|
| Strain | Dose | (1) | (2) | (3) | Nodule | PSD | (4) | (5) |
|  |  | 41,5 | 3,40 | 10,7 | 4 (6) | 4 | 0 | 8 |
| 15/5 | $6,3 \times 10^8$ | 41,3 | 2,20 | 9,7 | 4 | 2 | 0 | 9 |
|  |  | 41,7 | 2,60 | 18,0 | 4 | 4 | 0 | 9 |
|  |  | 40,4 | 0,52 | 3,7 | NR (7) | 0 | 0 | 5 |
| $D_1$ | $1,1 \times 10^9$ | 40,3 | 0,59 | 3,5 | NR | 0 | 0 | 5 |
|  |  | 40,7 | 0,95 | 4,9 | NR | 0 | 0 | 7 |
|  |  | 41,6 | 0,67 | 3,1 | NR | 0 | 0 | 5 |
| $D_5$ | $1 \times 10^9$ | 40,9 | 1,30 | 5,0 | NR | 0 | 0 | 5 |
|  |  | 40,5 | 1,40 | 3,7 | NR | 0 | 0 | 8 |
|  |  | 40,0 | 0,48 | 1,8 | NR | 0 | 0 | 8 |
| $Rv_1$ | $5,3 \times 10^8$ | 40,1 | 0,83 | 3,9 | 2 | 2 | 0 | 7 |
|  |  | 40,1 | 1,33 | 4,3 | 2 | 1 | 0 | 9 |
|  |  | 40,9 | 3,24 | 7,7 | 2 | 2 | 0 | 8 |
| $Rv_4$ | $1,1 \times 10^9$ | 41,0 | 1,73 | 9,3 | 4 | 2 | 0 | 9 |
|  |  | 40,7 | 1,41 | 9,3 | 4 | 2 | 0 | 9 |
|  |  | 40,9 | 2,80 | 4,3 | 4 | 3 | 0 | 8 |
| $Rv_6$ | $1 \times 10^9$ | 40,6 | 1,82 | 4,4 | 4 | 1 | 0 | 6 |
|  |  | 40,9 | 2,52 | 6,1 | 4 | 3 | 0 | 7 |

(1) Thermal acmes, in degrees Celcius; average temperature of the animals before injection = 39,5° C.
(2) Maximum thickness of the skin fold, in cm; average skin fold before injection = 0,27 cm
(3) Weight of the right prescapular ganglion, in g
(4) Other samplings: spleen, mesenteric ganglion, hepatic ganglion, liver, *vesicula fellea*, kidneys, testicles, epididymis, *vesicula seminalis*
(5) "O" Agglutination in microtechnique; the numbers indicate the highest positive dilution with 1 = 1/10, 2 = 1/20, 3 = 1.30 - Average before injection: 2,7
(6) Number of Salmonella isolated: - = absence of *Salmonella*; 1 = 1 to 5 bacteria; 2 = 6-25; 3 = 26-125; 4 = 125
(7) NR = not locatable and hence not taken up

(6) Virulence tests on ewes.

Two batches of Prealpes-Lacaunes ewes were vaccinated by sub-cutaneous injection on the ribs behind the left elbow, either with $D_5$ bacteria, or with $Rv_6$ bacteria. A third batch was composed of unvaccinated ewes.

The local reactions at the site of injection of the vaccine were evaluated by the thickness of the skin fold on the days indicated in the table, and by the formation or not of an open abscess.

| Vaccination | | Skin fold (in cm) on day x after vaccination (1) | | | | Open abscess |
|---|---|---|---|---|---|---|
| Strain | Dose | 7 | 14 | 21 | 27 | Total |
| Controls |  | 0,25 | — | — | — | — |
| $D_5$ | $7,3 \times 10^8$ | 1,12 | 0,49 | 0,30 | 0,28 | 0/18 |
| $Rv_6$ | $7 \times 10^8$ | 2,30 | 1,58 | 0,78 | 0,61 | 5/18 |

(1) Average on batches of 18 animals.

The ewes were fertilized 36 days later. A part of the animals which started gestation is used for testing the immunogenicity of the vaccine strains (see example 7). The other part enabled verification that the vaccinated ewes one month approximately before the start of gestation had then a normal gestation and did not excrete vaccinal bacteria on giving birth.

The characteristics for the latter are summarized in the following table. These results show that vaccination by means of the mutant strains obtained according to the invention does not affect the course of gestation and that the mutant strains are not excreted by vaccinated ewes. The presence of still born among the vaccinated animals has no particular significance considering that the bacteriological examination of the lambs concerned was negative.

| Vaccination | | Excretion on giving birth | Sex | Weight | Viability | Bacteriology |
|---|---|---|---|---|---|---|
| Strain | Dose | (1) | (2) | (kg) | (3) | (4) |
| Controls |  | — | F | 2,5 | + |  |
|  |  |  | M | 3,5 | + |  |
|  |  | — |  |  |  |  |
|  |  |  | M | 3,5 | + |  |
|  |  |  | M | 3,2 | + |  |
| $D_5$ | $7,3 \times 10^8$ | — | F | 2,7 | + |  |
|  |  |  | F | 3,3 | + |  |
|  |  | — |  |  |  |  |
|  |  |  | F | 2,8 | — | — |
|  |  | — | M | 3,6 | + |  |
|  |  | — | M | 4,5 | + |  |
| $Rv_6$ | $7 \times 10^8$ |  | M | 3,7 | + |  |
|  |  |  | F | 3,5 | + |  |
|  |  | — |  |  |  |  |
|  |  |  | F | 2,7 | + |  |
|  |  |  | F | 4,5 | + |  |
|  |  |  | M | 4,2 | + |  |
|  |  | — | M | 3,9 | + |  |
|  |  |  | F | 2,9 | + |  |
|  |  |  | F | 1,7 | + |  |
|  |  | — |  |  |  |  |
|  |  |  | M | 1,6 | — | — |
|  |  |  | F | 2,6 | + |  |
|  |  | — |  |  |  |  |
|  |  |  | F | 2,5 | — | — |

(1) Vaginal swab and colostrum
(2) M = Male; F = Female
(3) + = survival 2 days after birth; — = still-born or survival ≦ 2 days
(4) Bacteriological examination only done on the non viable lambs; lung, spleen, liver were taken out; — = no Salmonella detected.

(7) Immunogenicity tests on ewes.

The test of the protective power was carried out on pregnant ewes forming part of the 3 batches of animals described in example 6.

One hundred and two days after the vaccination and 68 hours after the start of their pregnancy, these ewes were tested by the sub-cutaneous injection of $8 \times 10^9$

*Salmonella abortus ovis* 15/5 behind the right elbow. The table indicates, for the three experimental groups, the clinical and bacteriological results recorded.

It appears that in the table below, of the two vaccine strains tested, that which confers the best resistance to the test inoculation was the reverse strain $Rv_6$.

| Vaccination | | Average Duration of pregnancy | Parturition at term | Viable lambs | Bacteriology negative |
|---|---|---|---|---|---|
| Strain | Dose | (days) | total (1) | total (2) | total (3) |
| Controls | | 92 | 1/9 | 1/14 | 1/9 |
| $D_5$ | $7,3 \times 10^8$ | 117 | 4/9 | 4/13 | 4/9 |
| $Rv_6$ | $7,0 \times 10^8$ | 133 | 8/10 | 9/13 | 6/10 |

(1) Period of gestation > 140 days
(2) Viable lambs: survival > 2 days after parturition
(3) Negative bacteriology: absence of Salmonella detectable in the vaginal mucus, the colostrum (if possible); and in the still-born or nonviable foeti; lung, spleen, gastric liquid, brain.

Appreciation of the level of protection thus conferred on the sheep had to take into consideration the severity of the immunogenicity test used. In fact, the sheep were tested at half-term, the period of maximum sensitivity to abortive infections; the test thus carried out caused eight control sheep out of 9 to abort, whereas the percentage of abortions observed in nature rarely exceeds 50% of the total pregnant sheep. The results of these tests should hence lead to a protective effect which is even much more distinct against infection in natura.

The following examples relates to the immunogenic properties of $Rv_6$, with respect to an infection caused by *Salmonella abortus ovis* and to an infection caused by *Salmonella typhimurium.*

The immunogenic properties of the strain $Rv_6$ have been tested with respect to an infection caused by the two serotypes of Salmonella which are the most frequently isolated strains in bovin pathology. These two strains are *Salmonella typhimurium* and *Salmonella dublin. Salmonella typhimurium,* and at a lower degree *Salmonella dublin,* are also pathogen for most of domestic animals and for man.

In order to test the immunogenicity of the strain $Rv_6$, with respect to a test inoculation of *Salmonella abortus ovis, Salmonella dublin* and *Salmonella typhimurium,* a protocol similar to the one above described under paragraph (4), has been used.

$CD_1$ female mice are vaccinated with $1.10^8$ bacteria of strain $Rv_6$, by the subcutaneous route, in the neck. Then, they are submitted to test infections as follows.

A third of the vaccinated mice are inoculated by the plantar subcutaneous route, with bacteria of the strain *Salmonella abortus ovis* (15/5), a third of mice are inoculated with the bacteria of the strain *Salmonella dublin* (the strain of *Salmonella dublin* used is the strain recorded under n. 9676 in the National Collection of Type Cultures), and the last third of mice is inoculated with the bacteria of the strain *Salmonella typhimurium* (C5).

At the same time, unvaccinated mice, which are used as control animals being inoculated with *Salmonella abortus ovis,* a third of the control animals being inoculated with *Salmonella dublin,* the last third of control animals being inoculated with *Salmonella typhimurium.* Two doses of the tested bacteria (*Salmonella abortus ovis, Salmonella dublin* and *Salmonella typhimurium*) are used and are respectively of about $1 \times 10^6$ (low dose) and of about $1 \times 10^8$ (high dose) per animal.

The fact of using two doses of test infection enables to obtain two kinds of results: mortality rate and level of splenic infection. The surviving mice are autopsied 4 days after the test infection at the acme of the splenic infection of mice which have been inoculated with *Salmonella typhimurium.*

The results are gathered in the table hereunder.

| | | Vaccinated animals (1) | | Control animals | |
|---|---|---|---|---|---|
| Strains | Doses of test inoculation (per animal) | Infected spleens / Cultivated spleens | Splenic infection $\left(\log X \pm \frac{s}{\sqrt{n}}\right)$ | Infected spleens / Inhibited spleens | Splenic infection (2) $\left(\log X \pm \frac{s}{\sqrt{n}}\right)$ |
| *Salmonella abortus ovis* | $7 \times 10^5$ | 6/10 | 1,87 ± 0,35 | 10/10 | 4,77 ± 0,23 |
| (15/5) | $7 \times 10^7$ | 10/10 | 4,30 ± 0,31 | 10/10 | 6,66 ± 0,19 |
| *Salmonella* | $1 \times 10^6$ | 8/10 | 1,22 ± 0,22 | 8/10 | 0,93 ± 0,22 |
| *dublin* (9676) | $1 \times 10^8$ | 10/10 | 3,80 ± 0,18 | 8/10 | 4,85 ± 0,16 |
| *Salmonella* | $9 \times 10^5$ | 9/10 | 1,45 ± 0,14 | 10/10 | 4,63 ± 0,37 |
| *typhimurium* (C5) | $9 \times 10^7$ | 10/10 | 4,90 ± 0,27 | (3) | (3) |

(1) Vaccinated animals per subcutaneous route (in the neck) with $1 \times 10^8$ bacteria $Rv_6$ per animal.
(2) Average of the decimal logarithms of the number of viable Salmonella in the infected slpeens.
(3) All the animals are dead.

The results show that the protection of vaccinated animals with respect to the test infection with *Salmonella dublin* is weak.

As to the test infection with *Salmonella typhimurium* the vaccination with the reverse strain $Rv_6$ of *Salmonella abortus ovis* protects efficiently the $CD_1$ mice.

In that case, the differences with respect to the mortality rate and splenic infection which can be noted between vaccinated animals and unvaccinated animals used as controls, are highly significant.

The results as to the protection conferred by vaccination with $Rv_6$, with respect to *Salmonella typhimurium* can be compared with the results obtained with respect to *Salmonella abortus ovis.*

These results show that the administration of the strain $Rv_6$ of *Salmonella abortus ovis* could be an efficient immunogenic agent against other kinds of serotypes whose antigenic structure is similar to the antigenic structure of *Salmonella typhimurium.* The phase "similar structure" is familiar for a man skilled in the art.

We claim:

1. A vaccine composition which comprises a biologically acceptable carrier and an alive, reverse, mutant genetically stable strain of *Salmonella abortus ovis* which is non-virulent in vivo, and immunogenic with respect to wild *Salmonella abortus ovis* and *Salmonella typhimurium.*

2. The vaccine composition of claim 1 wherein the strain is from that deposited with the Institut Pasteur, National Collection, Paris, France, under No. I-097.

3. The vaccine composition of claim 1 wherein the strain is capable of growing on the culture medium having a high content of streptomycin.

4. The vaccine composition of claim 1 wherein the strain is a strain whose growth is inhibited by a concentration of streptomycin from about 5 to about 10 microgram/ml.

5. The vaccine composition of claim 1 wherein the strain is a mutant of a streptomycin-dependent strain which is capable of growing in a medium containing about 50 micrograms per ml of streptomycin.

6. The vaccine composition of claim 1 which comprises from about $1 \times 10^7$ to about $10^{10}$ of bacteria.

7. The vaccine composition of claim 1 which is free of other microorganisms which are sensitive to streptomycin.

8. The vaccine composition of claim 1 wherein the strain is identifiable by a positive Voges-Proskauer test.

9. The vaccine composition of claim 1 which is freeze-dried.

10. The vaccine composition of claim 1 wherein the strain is a chromosomal mutant.

11. The method of immunization of a small ruminant animal susceptible to infection by salmonellosis caused by *Salmonella abortus ovis*, *Salmonella typhimurium* or *Salmonella dublin*, which comprises administering to such ruminants a dose sufficient to cause an immune response, a vaccine which comprises a biologically acceptable carrier and an alive, reverse, mutuant genetically stable strain of *Salmonella abortus ovis* which is non-virulent in vivo, and immunogenic with respect to wild *Salmonella abortus ovis* and *Salmonella typhimurium* and conferring immunity to the animal against said infection.

12. The method of claim 11 wherein the ruminant is sheep.

13. The method of claim 12 wherein the ruminant is selected from the group consisting of rams, ewes and lambs.

14. The method of claim 11 wherein the composition is freeze-dried.

15. The method of claim 11 wherein the dosage administered is in the range of about $1 \times 10^7$ and $7 \times 10^8$ of living bacteria.

16. The method of claim 11 which comprises determining that immunity has been conferred to the animal by testing for the presence of Salmonella and determining the absence of detectable Salmonella.

* * * * *